US00PP28218P2

(12) United States Plant Patent
Fouillet

(10) Patent No.: US PP28,218 P2
(45) Date of Patent: Jul. 25, 2017

(54) APPLE TREE NAMED 'R201'

(50) Latin Name: *Malus domestica*
Varietal Denomination: R201

(71) Applicant: International Fruit Obtention (IFO) GIE, Seiches sur le Loir (FR)

(72) Inventor: Valérie Fouillet, Saint Sylvain d'Anjou (FR)

(73) Assignee: International Fruit Obtentions, Seiches sur le Loir (FR)

( * ) Notice: Subject to any disclaimer, the term of this patent is extended or adjusted under 35 U.S.C. 154(b) by 0 days.

(21) Appl. No.: 14/999,021

(22) Filed: Mar. 18, 2016

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Michelle Bos Legal LLC

(57) ABSTRACT

'R201' apple tree is a new variety selected for its distinctive red-fleshed fruit, which is well-suited for the fresh market.

5 Drawing Sheets

Latin name: *Malus domestica.*
Variety denomination: 'R201'.

BACKGROUND OF THE VARIETY:

'R201' is a new and distinct variety of apple tree (*Malus domestica*) obtained from a controlled cross of 'MNR33S1A51' (female parent, not patented)×'Galaxy' (male parent, U.S. Plant Pat. No. 6,955) carried out at Seiches sur le Loir, France in 2006. Seeds obtained from the cross were planted at Seiches sur le Loir, and 'R201' was selected from the resulting seedlings for propagation and further observation. 'R201' was first asexually propagated by grafting at Seiches sur le Loir in 2011, and has since been observed to remain true to type over successive asexually propagated generations.

BRIEF DESCRIPTION OF THE VARIETY

'R201' apple tree is distinguished by its red-fleshed fruit. 'R201' is distinguished from its parents as shown in Tables 1 and 2 below.

TABLE 1

Comparison of 'R201' to 'MNR33S1A51'

| Characteristic | 'R201' | 'MNR33S1A51' |
|---|---|---|
| Fruit Size | Larger, avg. 218 g | Smaller, avg. 156 g |
| Flesh Color | Red (RHS 47A) | Dark pink-red (RHS 53C) |
| Skin Color | Dark purple brown (RHS 59A), solid flush, weakly defined stripes, moderate russeting | Dark purple brown (RHS 187A), solid flush, no striping, more russeting |

TABLE 2

Comparison of 'R201' to 'Galaxy'

| Characteristic | 'R201' | 'Galaxy' |
|---|---|---|
| Flesh color | Red (47A) | Cream |
| Skin color | Dark purple brown (RHS 59A) | Dark purple red (43A) |
| Harvest time | 5 weeks after 'Galaxy' | Mid- to late-season |

TABLE 2-continued

Comparison of 'R201' to 'Galaxy'

| Characteristic | 'R201' | 'Galaxy' |
|---|---|---|
| Amount of russet | More prone to russeting in stem cavity and on fruit | Less prone to russeting in stem cavity and on fruit |
| Flavor | Sweet, strawberry | Sweet |

BRIEF DESCRIPTION OF THE PHOTOGRAPHS

The accompanying photographs of the 'R201' variety were taken in 2015 at Seiches sur le Loir, France.

DETAILED BOTANICAL DESCRIPTION OF THE VARIETY

Figure 1:
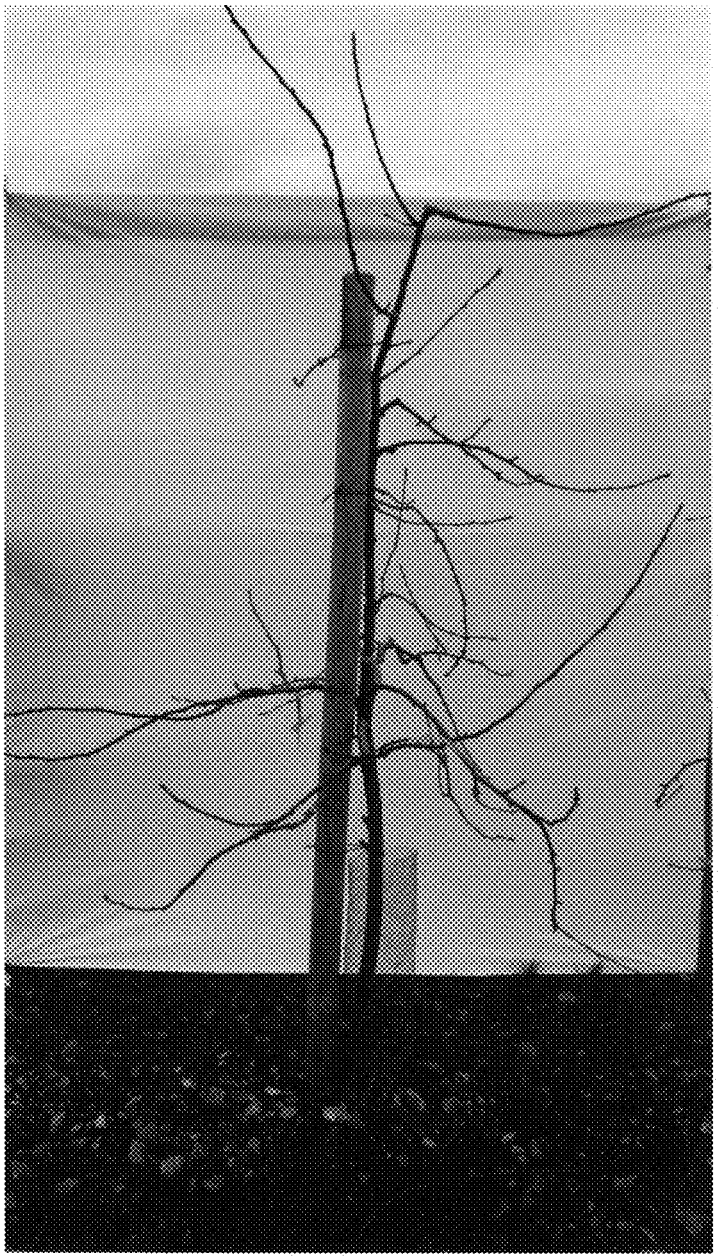
FIG. 1 is a photograph of a dormant 'R201' apple tree.
Figure 2:
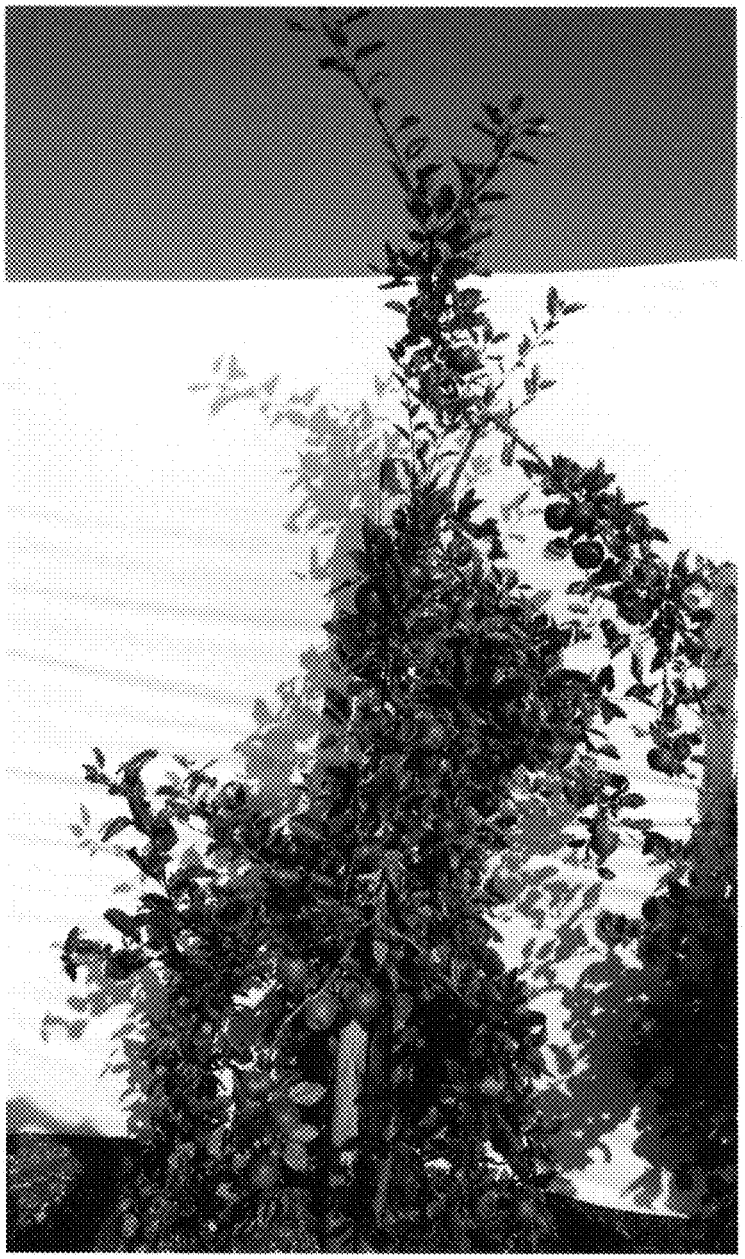
FIG. 2 is a photograph of an 'R201' apple tree with leaves and fruit.
Figure 3:
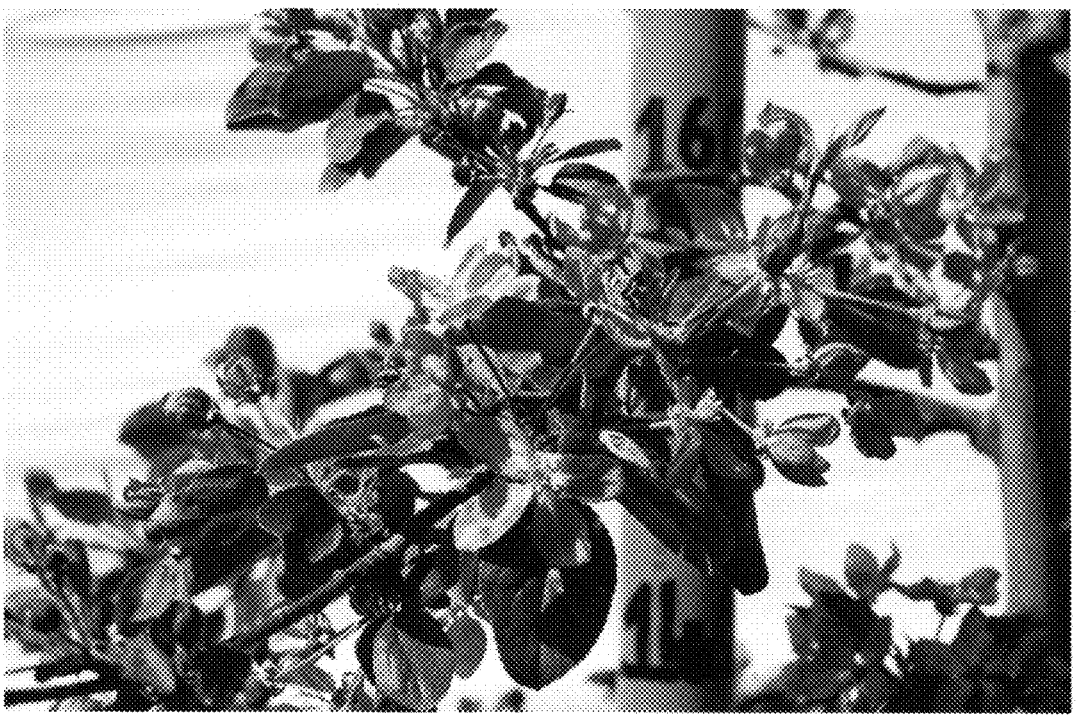
FIG. 3 is a photograph of flowers of an 'R201' apple tree.
Figure 4:
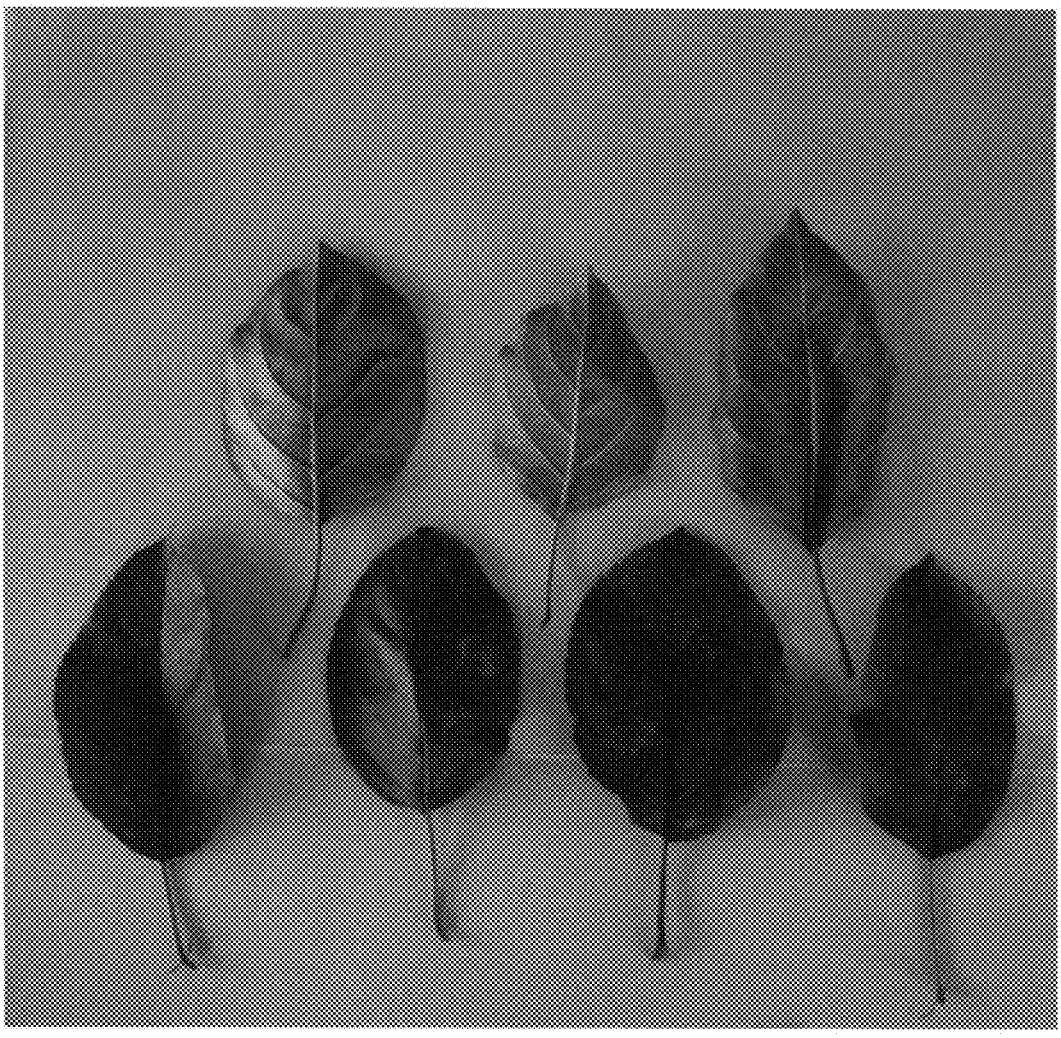
FIG. 4 is a photograph of leaves of an 'R201' apple tree.
Figure 5:
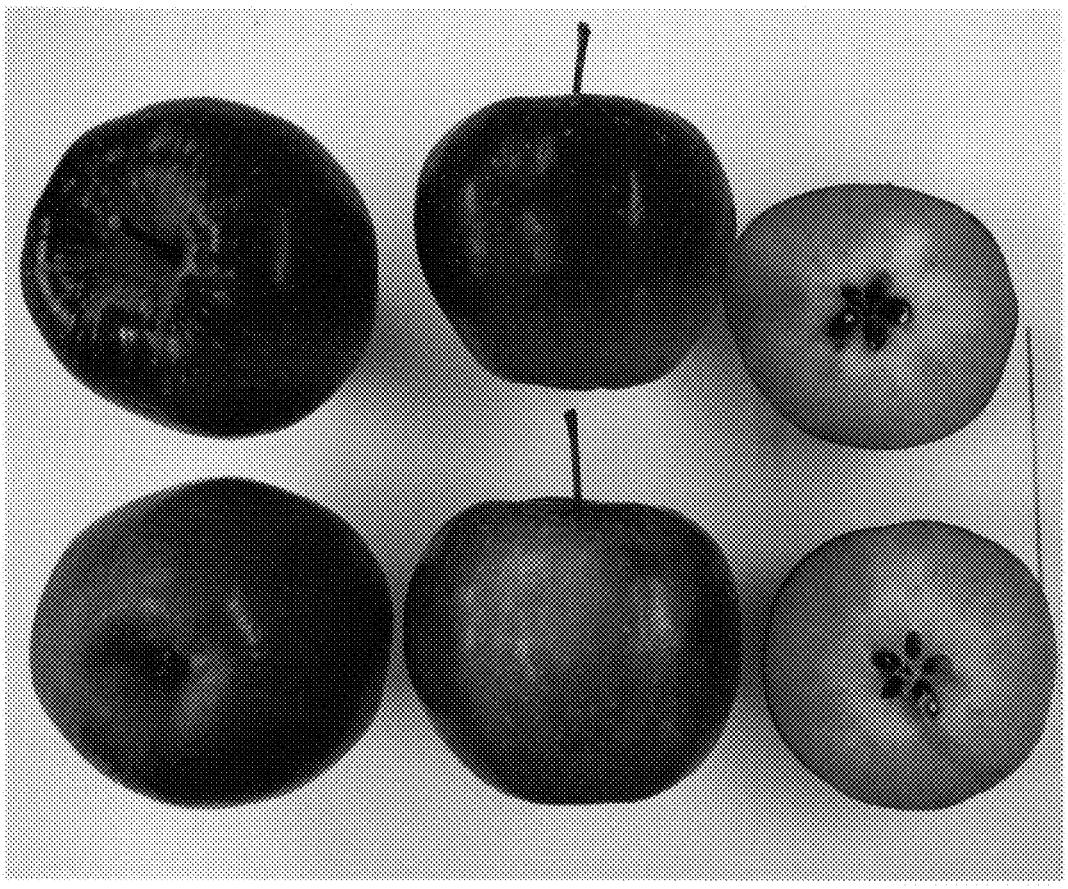
FIG. 5 is a photograph of 'R201' whole and sectioned apples.

The following detailed botanical description is based on observations made at Seiches sur le Loir, France during the 2015 growing season, of three year old trees grown on Pajam®2 'Cepiland' rootstock (U.S. Plant Pat. No. 7,715). All colors are described according to The Royal Horticultural Society Mini Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Medium.

*Type.*—Ramified.

*Habit.*—Drooping.

*Height*.—Approximately 2 m.
*Trunk diameter* (*at* 30 *cm above the graft*).—32 mm.
*Bark texture*.—Smooth.
*Bark color*.—Grey N200C.

Branch (fruiting branches located at around 1 m above the graft union):
*Length*.—108 cm.
*Diameter*.—15 mm.
*Crotch angle*.—50°.
*Bark color*.—Grey N200C.
*Lenticel length*.—1 mm.
*Lenticel color*.—Light yellow 20A.
*Number of lenticels per cm*$^2$.—3.

One year old shoot:
*Length*.—26 cm.
*Color*.—Dark brown 200A.
*Pubescence*.—Weak.
*Thickness*.—4 mm.
*Internode length*.—44 mm.
*Number of lenticels per cm*$^2$.—4.

Flower buds:
*Quantity per spur*.—3 to 5.
*Shape*.—Conical.
*Length*.—15 mm.
*Diameter*.—9 mm.
*Color*.—Purple brown 181A.

Flowers:
*Diameter of fully open flower*.—5 cm.
*Relative position of petal margin*.—Not touching.
*Number per cluster*.—6.
*Date of first bloom*.—April 17 (2015 growing season).
*Date of full bloom*.—April 22 (2015 growing season).
*Pollination requirement*.—'Gala', 'Granny Smith', and 'Golden Delicious' are suitable pollinators.

Petals:
*Number per flower*.—5.
*Shape*.—Oval.
*Length*.—24 mm.
*Width*.—15 mm.
*Apex*.—Rounded.
*Base*.—Acute.
*Margin*.—Smooth.
*Color of upper surface*.—Pink 63B.
*Color of lower surface*.—Purple pink N74C.

Pistils:
*Size*.—8 mm.
*Color*.—Orange brown 173C.

Stigma:
*Size*.—0.5 mm.
*Color*.—Brown N199C.

Style:
*Size*.—7 mm.
*Color*.—Orange brown 173C.

Ovary:
*Size*.—3 mm.
*Color*.—Envelope dark green 144A; ovules yellow green 145C.

Anthers:
*Quantity*.—16.
*Size*.—1 mm.
*Presence of pollen*.—Present.
*Color of pollen*.—Light yellow 4D.

Pedicel:
*Length*.—30 mm.
*Diameter*.—1 mm.
*Color*.—Brown green 152B.

Sepals:
*Quantity*.—5.
*Color*.—Green 139C.
*Shape*.—Pointed.
*Margin*.—Hairy.

Leaves:
*Shape*.—Elliptical.
*Length*.—100 mm (without stalk).
*Width*.—56 mm.
*Length/width ratio*.—1.8.
*Blade margin*.—Biserrate.
*Apex*.—Acute to caudate.
*Base shape*.—Acute.
*Color of upper surface*.—Dark green 137A.
*Color of lower surface*.—Brown N199A; veins dark purple 59A.
*Attitude in relation to shoot*.—Outwards.

Petiole:
*Length*.—33 mm.
*Diameter*.—1 mm.
*Color*.—Purple brown 181A.

Fruit:
*Quantity per cluster*.—1 to 3.
*Diameter*.—78 mm.
*Weight*.—218 g.
*Height*.—67 mm.
*Width*.—78 mm.
*Height to width*.—0.85.
*General shape in profile*.—Globose.
*Position of maximum diameter*.—Above equator.
*Ribbing*.—Moderate.
*Crowning at calyx end*.—Moderate.
*Size of eye*.—Medium.
*Aperture of eye*.—Closed.
*Length of sepal*.—Medium.
*Bloom of skin*.—Strong.
*Greasiness of skin*.—Absent.
*Amount of over color*.—Large.
*Over color of skin*.—Dark purple brown 59A.
*Intensity of over color*.—Dark.
*Pattern of over color*.—Solid flush.
*Amount of russet around stalk cavity*.—Large.
*Amount of russet on cheeks*.—Moderate.
*Area of russet around eye basin*.—Small.
*Length of stalk*.—31 mm.
*Thickness of stalk*.—2 mm.
*Depth of stalk cavity*.—Medium.
*Width of stalk cavity*.—Medium.
*Depth of eye basin*.—Medium.
*Width of eye basin*.—Medium.
*Firmness of flesh*.—Medium.
*Flesh texture*.—Medium to rough.
*Aroma, flavor*.—Sweet, berry flavors.
*Juiciness*.—Medium.
*Brix*.—15.
*Flesh color*.—80% red 47A; 20% white 155C.
*Stem color*.—Dark purple brown 187A.

Seeds:
*Quantity per fruit*.—11.
*Shape*.—Oval, medium thick.
*Color*.—Dark brown 200A.

Harvest:
*Time for harvest*.—Late, similar to 'Braeburn'.
*Number of picks*.—2 to 3.
*Fruit load per tree*.—Average 92 fruits.

Disease resistance/susceptibility: Resistant to scab.
Market use: Fresh consumption.

I claim:

1. A new and distinct apple tree substantially as described and illustrated herein.

* * * * *